United States Patent [19]  [11] 3,950,408
Chamberlin et al.  [45] Apr. 13, 1976

[54] PROCESS FOR PREPARING [1-OXO-2-CYCLOPENTYL (OR 2-ISOPROPYL)-2-METHYL-6,7-DICHLORO-5-INDANYLOXY] ACETIC ACID

[75] Inventors: Earl M. Chamberlin, Westfield; Warren K. Russ, Jr., Piscataway; George G. Hazen, Westfield, all of N.J.

[73] Assignee: Merck & Co., Inc., Rahway, N.J.

[22] Filed: Feb. 15, 1974

[21] Appl. No.: 442,691

[52] U.S. Cl. ...... 260/520 D; 260/473 F; 260/473 G; 260/521 H; 260/559 B; 260/592; 424/308; 424/317; 424/324; 260/590 R
[51] Int. Cl.$^2$.......................................... C07C 65/20
[58] Field of Search............... 260/473 G, 520, 590

[56] References Cited
FOREIGN PATENTS OR APPLICATIONS
267,940   6/1928   United Kingdom................ 260/590
288,441   4/1928   United Kingdom................ 260/590

OTHER PUBLICATIONS
March, "Advanced Organic Chemistry," McGraw–Hill Co., (N.Y.), 1968, pp. 406–416.
Beilstein, Band VII, p. 360 (1925).
Fuson et al., J. Am. Chem. Soc., 60 2935 (1938).

Primary Examiner—John F. Terapane
Attorney, Agent, or Firm—Michael C. Sudol, Jr.; Rudolph J. Anderson; J. Jerome Behan

[57] ABSTRACT
Process for preparing [1-oxo-2-cyclopentyl(or 2-isopropyl)-2-methyl-6,7-dichloro-5-indanyloxy]acetic acid, pharmaceutically acceptable salt, ester and amide derivatives thereof and intermediate 5-ether derivatives thereof comprising reacting under Friedel-Crafts conditions a 2-cyclopropyl-or 2-isopropylpropionyl halide or an anhydride thereof with an ether derivative of 2,3-dichlorophenol; and reacting the resulting propiophenone with formaldehyde in the presence of acid to yield the desired indanone.

5 Claims, No Drawings

PROCESS FOR PREPARING [1-OXO-2-CYCLOPENTYL (OR 2-ISOPROPYL)-2-METHYL-6,7-DICHLORO-5-INDANYLOXY] ACETIC ACID

BACKGROUND OF THE INVENTION

This invention relates to processes for the preparation of [1-oxo-2-cyclopentyl(or 2-isopropyl)-2-methyl-6,7-dichloro-5-indanyloxy]acetic acid, (I, below) and to the nontoxic phamaceutically acceptable salt, ester and amides thereof:

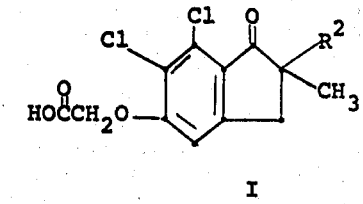

I wherein $R^2$ is cyclopentyl or isopropyl.

This invention also relates to useful intermediates in the preparation of I having the structures:

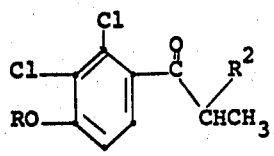

III

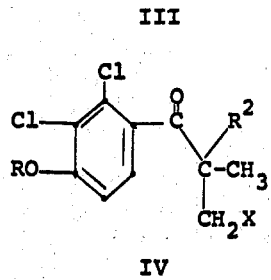

IV

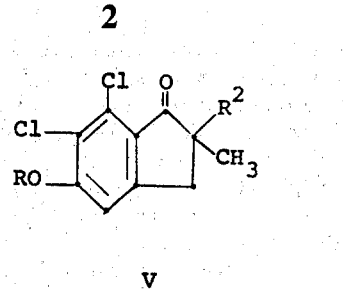

V wherein $R^2$ is cyclopentyl or isopropyl and R is $CH_2COOH$, $R^1$ or $CH_2COOR^1$, and wherein $R^1$ is lower alkyl or halo lower alkyl such as methyl, ethyl, isopropyl, trifluoromethyl, butyl, propyl and the like; aryl such as phenyl and nuclear substituted derivatives thereof such as nitrophenyl, tolyl, xylyl, ethylphenyl and the like; aralkyl and nuclear substituted aralkyl having from 7 to about 20 carbon atoms such as benzyl, p-chlorobenzyl, p-nitrobenzyl and the like; and wherein X is OH, halo, and acid ester moieties such as trifluoroacetate, tosylate, acetate and the like.

The indanones of structure I and the nontoxic pharmaceutically acceptable salt, ester and amide derivatives, have diuretic, saluretic and uricosuric activity.

Thus, it is an object of the present invention to provide a specific, unified process for the preparation pf [1-oxo-2-cyclopentyl(or 2-isopropyl)-2-methyl-6,7-dichloro-5-indanyloxy]acetic acid and the nontoxic pharmaceutically acceptable salt, ester and amide derivatives thereof. It is also an object of the present invention to provide useful intermediates (III, IV, and V, above-described) which are involved in the process of this invention.

DETAILED DESCRIPTION OF THE INVENTION

The process of the present invention may most conveniently be described by the following schematic overview:

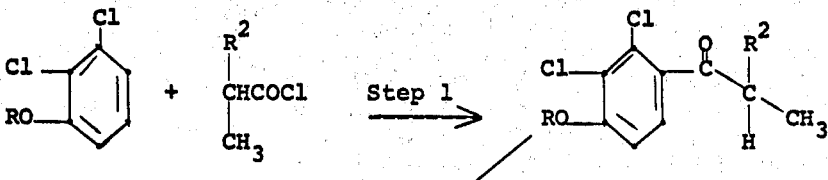

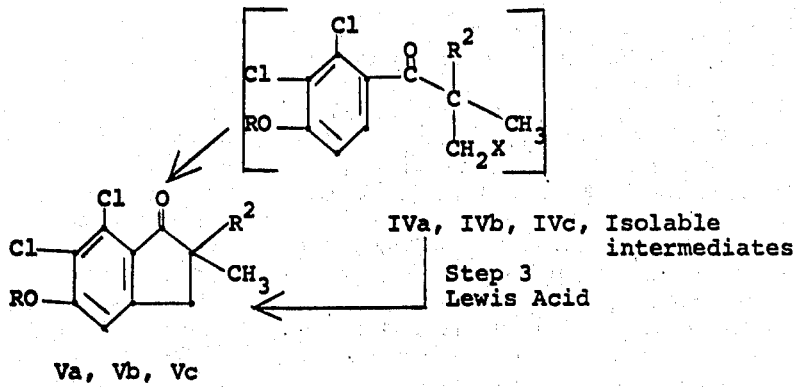

wherein $R^2$, R, $R^1$ and X have previously been defined and wherein for the structures I$a$, III$a$, IV$a$, and V$a$ R is $R^1$; for structures I$b$, III$b$, IV$b$ and V$b$ R is $CH_2COOH$; and for structures I$c$, III$c$, IV$c$ and V$c$ R is $CH_2COOR^1$. There is no criticality as to the precise identity of $R^1$ other than that it be compatible with the desired course of reaction since the function of $R^1$ is merely that of a blocking or protective group.

In words relative to the above diagram, a 2-isopropyl or 2-cyclopentyl-propionyl halide (II) or an anhydride thereof and a 2,3-dichlorophenol ether (I$a$, such as 2,3-dichloroanisole) or 2,3-dichlorophenoxy acetic acid (I$b$) or an ester thereof (I$c$) is reacted (Step 1) under Friedel-Crafts conditions in the presence of a suitable catalyst such as aluminum trichloride and the like in a solvent such as methylene chloride or the like to yield the corresponding propiophenone (III$a$, III$b$, or III$c$) which is reacted (Step 2) with formaldehyde (paraformaldehyde) in the presence of acid to produce by way of the isolable intermediate (IV$a$, IV$b$, or IV$c$) the desired indanone (V$a$, V$b$, or V$c$).

Alternately, the hydroxymethyl intermediate or the corresponding halide or ester derivative thereof (IV$a$, IV$b$, IV$c$) may be isolated and subjected to a distinct cyclialkylation step (Step 3) in the presence of a suitable dehydrating agent, a dehydroacylating agent or generically any Lewis Acid to yield the corresponding indanone (V$a$, V$b$, or V$c$).

It will be noted that the indanone of structure V$b$ corresponds to I, above-depicted, and that the indanones of V$c$ are embraced by the definition of pharmaceutically acceptable esters of I. The ether derivatives, V$a$, may be converted to V$b$ or V$c$ by hydrolysis and reaction with halo acetic acid or with a halo acetic acid ester, respectively; further the structure of V$c$ is convertible to V$b$ by hydrolysis.

In further description of Step 1, suitable catalyst are any of those recognized as Friedel-Crafts catalysts such as aluminum trichloride, $SnCl_4$, $AlBr_3$, $BF_3$ and the like. The reaction solvent and the temperature of reaction are not considered critical aspects of the instant unified scheme of synthesis inasmuch as any solvent which is inert or substantially inert to the reactants and product may be employed. In this regard it has been found that solvents such as methylenechloride, 1,2-dichloroethane, carbon disulfide, syn-tetrachlorethane and the like are particularly preferred. The reaction temperature may range from about 0° to about 50°C. and is preferably from about 0° to about 10°C. In Step 1, the molar ratio of reactants, dichlorophenoxy species: 2-substituted-propionyl halide may range from about 2:1 to about 1:4. The amount of catalyst may range from about 25 to about 200 mole & based on the dichlorophenoxy reactant; the range of 35 to 60 mole % is preferred.

With respect to Step 2, the molar ratio of the particular propiophenone (III$a$, III$b$, or III$c$, above) from Step 1 to formaldehyde, is in the range of from about 1:1 to about 1:10. The precise identity of the acid of Step 2 is not critical inasmuch as any strong organic or inorganic acid such as trifluoroacetic acid, methanesulfonic acid, borontrifluoride, $H_2SO_4$, HF, phosphoric and the like is operable. The most preferred acids are trifluoroacetic acid, $BF_3$ and $H_2SO_4$. Typically the molar ratio of the acid relative to the propiophenoneacid molar sum ranges from about 0.05 to an upper value of about 0.99 when the acid serves as the solvent, which is preferred. Other solvents may be employed, however, and may be selected from the group consisting of methylene chloride, benzene, toluene and the like. The temperature of reaction of Step 2 is typically in the range of from about 25° to about 150°C.; preferably the reaction is conducted at the relfux temperature of the solvent system, typically 80° to 120°C. The reaction of Step 2 is typically completed in from 3 to 18 hours.

Precise information relative to completion of the reaction with quantitative conversion of the propiophenone to the desired indanone is obtainable by monitoring the disappearance of the methyne proton and one-half of the aromatic protons with standard nuclear magnetic resonance (nmr) techniques.

Alternatively, Step 2 may be interrupted to isolate the intermediates, IV$a$, IV$b$ and IV$c$, for later cyclialkylation to the corresponding indanones according to Step 3. Quantitative conversion to the intermediates is indicated by standard nmr techniques to correspond to the disappearance of the methyne proton of the starting material (III$a$, III$b$, and III$c$). The intermediate, as the hydroxymethyl species or as the acid ester made available by the conditions of Step 2, may be converted as such to the ultimate indanone or may be converted to a halide or another ester such as tosylate, acetate or trifluoroacetate and the like prior to being subjected to the ring closure conditions of Step 3. The ring closure agents of Step 3 are generally selected from Lewis Acids such as trifluoroacetic acid, concentrated sulfuric acid, $BF_3$, HF, phosphonic acid and the like. Typically a solvent is not required since the acid serves as its own solvent, however, suitable solvents include any nonpolar, inert solvent such as methylene chloride, benzene, tolulene and the like. The temperature of reaction may range from about 0 to about 100°C., and preferably is from about 0° to about 25°C. The reaction typically requires from about 1 to about 5 hours and may be precisely followed, as noted above for Step 2, by standard nmr techniques.

The following Examples specifically illustrate but do not limit either the product or process aspects of the present invention. Further it is to be emphasized that while the Examples specifically illustrate the process invention in terms of discrete step such step-wise division is artificial and arbitrarily adopted as a means of furthering the description of the useful intermediate product aspects. For the reality the process aspect of the present invention relates to a unified scheme of synthesis of [1-oxo-2-cyclopentyl(or 2-isopropyl)-2-methyl-6,7-dichloro-5-indanyloxy]acetic acid and the nontoxic pharmaceutically acceptable salt, ester and amide derivatives thereof.

EXAMPLE 1

Preparation of 2,3-dichloro-4-methoxy-α-cyclopentyl propiophenone

In a 2 1. round-bottom -4-necked flask equipped with stirrer, reflux condenser with drying tube, thermometer and hopper for aluminum chloride are placed 2,3-dichloroanisole (137.0 g., 0.774 mole), 2-cyclopentyl propionyl chloride (137 g., 0.934 mole) and methylenechloride (600 ml.). The mixture is stirred, cooled to 5°C. and aluminum trichloride (114 g.) is added portionwise during a one hour interval while maintaining a temperature at 5°C. The mixture is heated and held at 25°C. for 16 hours. The resulting mixture is added to 1 1. of aqueous 1.5 molar HCl. The lower organic layer is separated; the aqueous phase is extracted with methylenechloride and the combined extracts are washed with a saturated aqueous solution of sodium chloride, 10 wt.

% aqueous sodium hydroxide solution and again with the saturated sodium chloride solution, dried over magnesium sulfate and evaporated at reduced pressure. The resulting green oil is dissolved in hot hexane (200 ml.) and on cooling 2,3-dichloro-4-methoxy-α-cyclopentyl propiophenone separates.

EXAMPLE 1a

Preparation of 2,3-dichloro-4-methoxy-α-isopropylpropiophenone

Following the procedure exactly as described in Example 1 except that an equivalent amount of 2-isopropylpropionyl chloride is substituted for the 2-cyclopentyl propionyl chloride, there is obtained 2,3-dichloro-4-methoxy-α-isopropyl propiophenone.

EXAMPLE 2

Preparation of 2,3-dichloro-4-carboxymethoxy-α-cyclopentyl propiophenone

Following the procedure exactly as described in Example 1 except that the 2,3-dichloroanisole is replaced by 2,3-dichlorophenoxy actic acid (171.0 g., 0.773 moles), there is obtained 2,3-dichloro-4-carboxymethoxy-α-cyclopentyl propiophenone.

EXAMPLE 2a

Preparation of 2,3-dichloro-4-carboxymethoxy-α-isopropylpropiophenone

Following the procedure exactly as described in Example 1a except that the 2,3-dichloroanisole is replaced by an equivalent amount of 2,3-dichlorophenoxy acetic acid, there is obtained 2,3-dichloro-4-carboxymethoxy-α-isopropyl propiophenone.

EXAMPLE 3

Preparation of 2,3-dichloro-4-(ethylcarboxymethoxy)-α-cyclopentyl propiophenone

Following the procedure exactly as described in Example 1 except that the 2,3-dichloroanisole is replaced by 193 g., 0.775 moles of ethyl [2,3-dichlorophenoxy-]acetate there is obtained 2,3-dichloro-4-(ethylcarboxymethoxy)-α-cyclopentyl propiophenone.

EXAMPLE 4

Following the procedure exactly as described in Example 1 and Example 1a except that the 2,3-dichloroanisole is replaced by an equivalent amount of (1,2-dichloro) ethoxybenzene and trifluoromethyl(2,3-dichlorophenoxy)-acetate respectively, there is obtained 2,3-dichloro-4-ethoxy (and trifluoromethyl carboxymethoxy)-α-cyclopentyl(and isopropyl)propiophenone, respectively.

EXAMPLE 5

Preparation of (1-oxo-2-cyclopentyl-2-methyl-6,7-dichloro5-indanyloxy) acetic acid Step A: Preparation of 2-cyclopentyl-2-methyl-5-methoxy-6,7-dichloro-1-indanone 1 Mole of 2,3-dichloro-4-methoxy-α-cyclopentyl propiopheone obtained from Example 1 and 1.3 moles of formaldehyde (taken as paraformaldehyde) and 1.1 of trifluoroacetic acid are refluxed and the disappearance of the methyne proton and finally one half of the aromatic protons is followed by assaying portions of the reaction mixture by nmr. Excess trifluoroacetic acid is removed under vacuum at 25°C. and the resulting crude product is freed of residual trifluoro acetic acid by dissolving in ether and washing with a saturated aqueous sodium bicarbonate solution until neutral. The ether solution is then dried with anhydrous magnesium sulfate, filtered and evaporated under vacuum to give 2-cyclopentyl-2-methyl-5-methoxy-6,7-dichloro-1-indanone.

Step B: Preparation of 1-oxo-2-cyclopentyl-2-methyl-6,7-dichloro-5-indanyloxy acetic acid 250 Grams of the 2-cyclopentyl-2-methyl-5-methoxy-6,7-dichloro-1-indanone is heated for 7 hours at 85°C. in 100 g. of pyridine hydrochloride to provide the 5-hydroxy species; thereafter 200 ml. of dimethylformamide, 100 g. of sodium carbonate, and 0.105 moles of chloroacetic acid is added. The resulting product is extracted with methylenechloride, isolated, and recrystallized from glacial acetic acid to provide (1-oxo-2-cyclopentyl-2-methyl-6,7-dichloro-5-indanyloxy)-acetic acid.

EXAMPLE 5a

Preparation of 1-oxo-2-methyl-2-isopropyl-6,7-dichloro-5-indanyloxy acetic acid

Following the procedure exactly as described in Example 5 except that an equivalent amount of 2,3-dichloro4-methoxy-α-isopropyl-propiophenone for Example 1a is substituted for the 2,3-dichloro-4-methoxy-α-cyclopentylpropiopheone there is obtained (1-oxo-2-cyclopentyl-2-methyl-2-isopropyl-6,7-dichloro-5-indanyloxy)acetic acid.

EXAMPLE 6

Preparation of 1-oxo-2-cyclopentyl(and 2-isopropyl)-2-methyl-6,7-dichloro-5-indanyl acetic acid Following the procedure exactly as described in Example 5, Step A except that an equivalent amount of 2,3-dichloro-4-carboxymethoxy-α-cyclopentyl propiophenone and 2,3-dichloro-4-carboxymethoxy-α-isopropyl propiophenone, respectively, is substituted for the 2,3-dichloro-4-methoxy-α-cyclopentyl-propiophenone there is obtained [1-oxo-2-cyclopentyl-2-methyl-6,7-dichloro-5-indanyloxy] acetic acid and [1-oxo-2-isopropyl-2-methyl-6,7-dichloro5-indanyloxy]acetic acid respectively.

Similarly, when an equivalent amount of the ethyl ester of Example 3 and the trifluoromethyl ester of Example 4, respectively, is substituted for propiophenone of Example 5, Step A, there is obtained ethyl (and trifluoromethyl) [1-oxo-2-cyclopentyl(and 2-isopropyl)- 2-methyl-6,7-dichloro-5-indanyloxy]acetate, respectively, which upon hydrolysis in 0.10 wt. % NaOH for 2 hr. at reflux yields after acidification, (1-oxo-2-cyclopentyl-(and 2-isopropyl)-2-methyl-6,7-dichloro-indanyloxy)-acetic acid.

EXAMPLE 6a

Preparation of 1-oxo-2-cyclopentyl (and 2-isopropyl)-2-methyl-6,7-dichloro-5-indanyloxy acetic acid Following the procedure exactly as described in Example 5 except that the 2,3-dichloro-4-methoxy-α- cyclopentyl-propiopheone is replaced by 2,3-dichloro-4-ethoxy-α-cyclopentyl propiophenone and 2,3-dichloro-4-ethoxy-α-isopropyl propiophenone, respectively, from Example 4 there is obtained (1-oxo-2-cyclopentyl-2-methyl-6,7-dichloro-5-indanyloxy) acetic acid and (1-oxo-2-isopropyl-2-methyl-6,7-dichloro-5-indanyloxy) acetic acid, respectively.

EXAMPLE 7

Preparation of 2,3-dichloro-4-methoxy-α-hydroxymethyl-α-cyclopentyl propiophenone 1 Mole of 2,3-dichloro-4-methoxy-α-cyclopentyl propiophenone, 1.3 moles of formaldehyde (taken as paraformaldehyde) and 1 l. of trifluoroacetic acid are refluxed and the disappearance of the methyne hydrogen proton is followed by assaying aliquots of the reaction mixture by nmr. Excess trifluoroacetic acid is removed under vacuum at 25°C. and the crude product is freed of residual trifluoroacetic acid by dissolving in ether and washing with a saturated aqueous sodium bicarbonate solution until neutral. Evaporation gives a mixture of 2,3-dichloro-4-methoxy-α-hydroxymethyl-α-cyclopentyl propiophenone and its trifluoroacetic acid ester, which mixture is dissolved in 1 l. of ethanol; 80 g. of sodium hydroxide is added and the solution is refluxed overnight, cooled and neutralized with 6N hydrochloric acid. After evaporation to 250 ml., 250 ml. of water and 2 l. of ether are added. The aqueous layer is removed and the ether evaporated to give, 2,3-dichloro-4-methoxy-α-hydroxymethyl-α-cyclopentyl propiophenone.

EXAMPLE 7a

Preparation of 2,3-dichloro-4-methoxy-α-hydroxymethyl-α-isopropyl propiophenone

Following the procedure exactly as described in Example 7 except that an equivalent amount of 2,3-dichloro-4-methoxy-α-isoproply propiophenone is substituted for the 2,3-dichloro-4-methoxy-α-cyclopentyl propiophenone there is obtained 2,3-dichloro-4-methoxy-α-hydroxymethyl-α-isopropyl propiophenone.

EXAMPLE 8

Following the procedure of Example 7 or 7a except that there is substituted for the 2,3-dichloro-4-methoxy-α-cyclopentyl propiophenone or 2,3-dichloro-4-methoxy-α-isopropyl propiophenone, respectively, an equivalent amount of the propiophenone obtained from Examples 2, 2a, 3, and 4, respectively there is obtained 2,3-dichloro-4-carboxymethoxy-α-cyclopentyl-α-hydroxymethyl-propiophenone; 2,3-dichloro-4-carboxymethoxy-α-isopropyl-α-hydroxymethyl propiophenone; 2,3-dichloro-4-(ethylcarboxymethoxy)-α-cyclopentyl-α-hydroxymethyl propiophenone; 2,3-dichloro-4-ethoxy(and trifluoromethylcarboxymethoxy)-α-cyclopentyl(and α-isopropyl)-α-hydroxymethyl propiophenone, respectively.

EXAMPLE 9

Preparation of (1-oxo-2-cyclopentyl-2-methyl-6,7-dichloro-5-indanyloxy)acetic acid Step A: Preparation of 2-cyclopentyl-2-methyl-6,7-dichloro-5-methoxy indanone 1 Mole of 2,3-dichloro-4-methoxy-α-cyclopentyl-α-hydroxymethyl-propiophenone obtained from Example 7 is added portionwise to 1 l. of stirred 96% sulfuric acid; the temperature is maintained at 20°C. Thereafter the temperature is adjusted to 25°C. and the mixture is stirred for 1 ½ hours. The resulting red solution is added dropwise to 6 l. of water with stirring and a gummy solid separates. After standing 16 hours, the solid is broken up and collected on a sintered glass filter; crystallization from 1 l. of ethanol gives 2-cyclopentyl-2-methyl-6,7-dichloro-5-methoxy indanone which melts at 111°-113°C.

Step B: Preparation of 1-oxo-2-cyclopentyl-2-methyl-6,7-dichloro-5-indanyloxy acetic acid 25.0 Grams of the 2-cyclopentyl-2-methyl-5-methoxy-6,7-dichloro-1-indanone is heated for 7 hours at 85°C. in 100 g. of pyridine hydrochloride to provide the 5-hydroxy species; thereafter 200 ml. of dimethylformamide, 100 g. of sodium carbonate, and 0.105 moles of chloroacetic acid is added. The resulting product is extracted with methylenechloride, isolated, and recrystallized from glacial acetic acid to provide (1-oxo-2-cyclopentyl-2-methyl-6,7-dichloro-5-indanyloxy)-acetic acid.

Exactly as described in Example 9, Step A, except that there is substituted for the 2,3-dichloro-5-methoxy-α-cyclopentyl-α-hydroxymethyl propiophenone an analogous α-hydroxymethyl propiophenone from Example 7a, or Example 8, respectively, the corresponding 2-cyclopentyl(or 2-isopropyl)-2-methyl indanone of the present invention is obtained following appropiate hydrolysis and acidification, as in Example 6, or hydrolysis and etherification, as described in Example 9, Step B.

Similar results are obtained as in Example 9 when the α-hydroxymethyl propiophenone species is replaced by a derivative thereof having the structure:

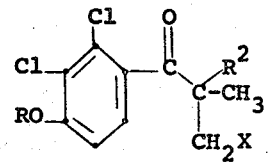

wherein R, R² and X have previously been defined. Such ester and halo derivatives (X is an acid ester moiety, or halo) are readily prepared from the α-hydroxymethyl species by methods well known in the art.

What is claimed is:
1. The process for preparing a compound of the formula:

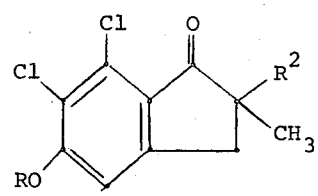

wherein $R^2$ is cyclopentyl or isopropyl; R is $CH_2COOH$, $R^1$ or $CH_2COOR^1$, and wherein $R^1$ is lower alkyl or halo lower alkyl selected from the group consisting of methyl, ethyl, isopropyl, trifluoromethyl, propyl and butyl; phenyl or substituted phenyl selected from the group consisting of nitrophenyl, tolyl, xylyl and ethylphenyl; benzyl or nuclear substituted benzyl selected from the group consisting of pchlorobenzyl and p-nitrobenzyl comprising the steps of:

a. reacting under Friedel-Crafts conditions wherein said conditions comprise the use of a Lewis acid catalyst selected from the group consisting of aluminum trichloride, $SnCl_4$, $AlBr_3$ and $BF_3$; and the use of an organic solvent which does not react with the reactants; and wherein said reaction is carried out at a temperature from about 0°C. to about 50°C; an ether derivative of 2,3-dichlorophenol of the formula:

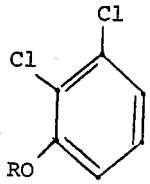

wherein R is a defined above and a 2-substituted propionyl halide of the formula:

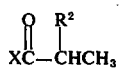

wherein $R^2$ is as defined above; and X is halo; wherein the molar ratio of the reactants may range from about 2:1 respectively to about 1:4 respectively; and wherein the amount of catalyst ranges from about 25 to about 200 moles % based on the ether derivative of 2,3-dichlorophenol; and b. reacting the resulting propiophenone of Step (a) with formaldehyde in the presence of an acid selected from the group consisting of the trifluoroacetic acid methanesulfonic acid, borontrifluoride, $H_2SO_4$, HF and phosphoric acid; wherein the molar ratio of the propiophenone of Step (a) to formaldehyde, is in the range of from about 1:1 to about 1:10; wherein the molar ratio of the acid relative to the propiophenone ranges from about 0.05 to about 0.99; and wherein the reaction is carried out at a temperature in the range of from about 25°C. to about 150°C.

2. The process of claim 1 wherein the ether derivative of 2,3-dichlorophenol is:

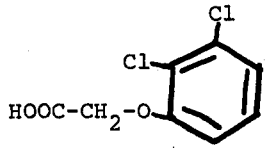

3. The process of claim 2 wherein X is chloro and the acid is trifluoroacetic, boron trifluoride, sulfuric, phosphoric, methanesulfonic, hydrofluoric, or aluminum trichloride.

4. A process for preparing a compound of the formula:

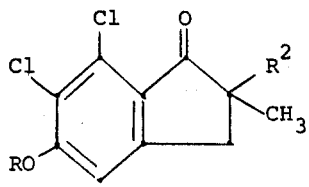

wherein $R^2$ is cyclopentyl or isopropyl; R is $CH_2COOH$, $R^1$ or $CH_2COOR^1$, and wherein $R^1$ is lower alkyl or halo lower alkyl selected from the group consisting of methyl, ethyl, isopropyl, trifluoromethyl, propyl and butyl; phenyl or substituted phenyl selected from the group consisting of nitrophenyl, tolyl, xylyl and ethylphenyl; benzyl or nuclear substituted benzyl selected from the group consisting of p-chlorobenzyl and p-nitrobenzyl; comprising reacting a propiophenone of the formula:

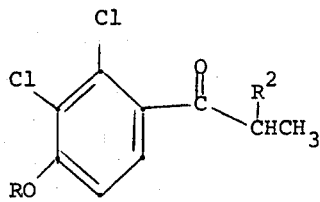

wherein R and $R^2$ are as defined above with formaldehyde in the presence of an acid selected from the group consisting of trifluoroacetic acid, methanesulfonic acid, borontrifluoride, $H_2SO_4$, HF and phosphoric acid; wherein the molar ratio of the propiophenone to formaldehyde is in the range of from about 1:1 to about 1:10; wherein the molar ratio of the acid relative to the propiophenone ranges from about 0.05 to about 0.99; and wherein the reaction is carried out in the temperature in the range of from about 25°C. to about 150°C.

5. A process for preparing (1-oxo-2-cyclopentyl-2-methyl-6,7-dichloro-5-indanyloxy)acetic acid and (1-oxo-2-isopropyl-2-methyl-6,7-dichloro-5-indanyloxy)-acetic acid comprising the steps of:

a. reacting the ether derivative of 2,3-dichlorophenol having the structure:

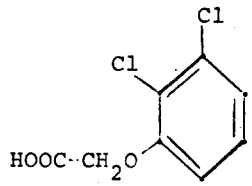

with a 2-cyclopentyl propionyl halide or 2-isopropyl propionyl halide, respectively, under Friedel-Crafts conditions; wherein said conditions comprise the use of a Lewis acid catalyst selected from the group consisting of aluminum trichloride, $SnCl_4$, $AlBr_3$ and $BF_3$; and the use of an organic solvent which does not react with the reactants; wherein said reaction is carried out at a temperature from about 0° to 50°C.; wherein the molar ratio of the reactants may range from about 2:1 respectively to about 1:4 respectively; and wherein the amount of catalyst ranges from about 25 to about 200 mole % based on the ether derivative of 2,3-dichlorophenol; and b. reacting the resulting propiophenone of Step a. with formaldehyde in the presence of acid selected from the group consisting of trifluoroacetic acid, methanesulfonic acid, borontrifluoride, $H_2So_4$, HF and phosphoric acid; wherein the molar ratio of the propiophenone of Step a.) to formaldehyde, is in the range of from about 1:1 to about 1:10; wherein the molar ratio of the acid relative to the propiophenone acid ranges from about 0.05 to about 0.99 and wherein the reaction is carried out in the temperature in the range of from about 25°C. to about 150°C.; to obtain the corresponding α-substituted propiophenone; and c. treating the product of Step (b) or a halide or ester derivative thereof with a Lewis Acid selected from the group consisting of trifluoroacetic acid, boron trifluoride, concentrated sulfuric acid, phosphoric acid and hydrofluoric acid at a temperature in the range of from about 0°C. to about 100°C. from about 1 hour to about 5 hours to effect ring closure.

* * * * *